United States Patent [19]

Haviv et al.

[11] Patent Number: 4,476,137
[45] Date of Patent: Oct. 9, 1984

[54] [1-(2-BENZOXAZOLYL)HYDRAZINO]ALKYL NITRILE DERIVATIVES

[75] Inventors: Fortuna Haviv, Deerfield; James D. Ratajczyk; Francis E. Fischer, both of Waukegan, all of Ill.

[73] Assignee: Abbott Laboratories, North Chicago, Ill.

[21] Appl. No.: 471,926

[22] Filed: Mar. 3, 1983

Related U.S. Application Data

[63] Continuation-in-part of Ser. No. 311,843, Oct. 16, 1981, abandoned.

[51] Int. Cl.³ .................. A61K 31/42; C07D 263/58
[52] U.S. Cl. ................................ 424/272; 548/161; 548/222; 548/483; 424/270; 424/274; 424/278
[58] Field of Search .................. 548/222; 424/272

[56] References Cited

U.S. PATENT DOCUMENTS

| | | | |
|---|---|---|---|
| 3,937,714 | 2/1976 | Barnett | 548/161 |
| 3,981,869 | 9/1976 | Ziemek | 548/180 |
| 4,178,451 | 12/1979 | Wade et al. | 424/270 |
| 4,319,026 | 3/1982 | Hedrich et al. | 548/222 |

OTHER PUBLICATIONS

Nagarajan, K., et al., Indian Journal of Chemistry, vol. 9, pp. 748-754, (1971).

*Primary Examiner*—Robert Gerstl
*Assistant Examiner*—S. A. Gibson
*Attorney, Agent, or Firm*—Gildo E. Fato; Martin L. Katz; Steven F. Weinstock

[57] ABSTRACT

Described are compounds of the formula

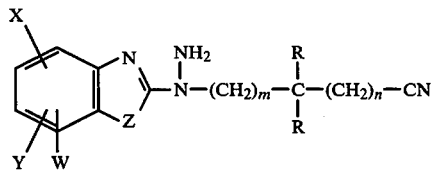

wherein R is hydrogen or loweralkyl, X, Y and W independently of one another denote hydrogen, halogen, loweralkyl, nitro, amino, amido, loweralkoxy, hydroxy, nitrile, methylsulfone, methylsulfoxide, methylmercapto, or trifluoromethyl; Z is oxygen, sulfur or —$CH_2$; n and m are each an integer from 0 to 6 inclusive, or pharmaceutically acceptable salts thereof.

The compounds are effective as anti-inflammatory agents.

19 Claims, No Drawings

[1-(2-BENZOXAZOLYL)HYDRAZINO]ALKYL NITRILE DERIVATIVES

BACKGROUND OF THE INVENTION

This application is a continuation-in-part application of application Ser. No. 311,843, filed Oct. 16, 1981 now abandoned.

The present invention provides compositions for the treatment of osteoarthritis, rheumatoid arthritis, type III hypersensitivity diseases, diseases in which polymorphonuclear leukocyte accumulation contributes to the pathology, and other inflammatory conditions. An antiinflammatory composition in dosage unit form is described.

SUMMARY OF THE INVENTION

The present invention is directed to compounds of the formula

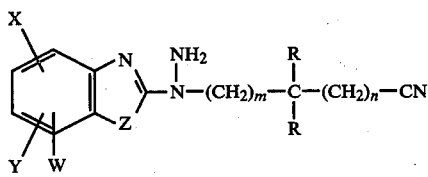

I wherein R is hydrogen or loweralkyl, X, Y and W independently of one another denote hydrogen, halogen, loweralkyl, nitro, amino, amido, loweralkoxy, hydroxy, nitrile, methylsulfone, methylsulfoxide, methylmercapto, or trifluoromethyl; Z is oxygen, sulfur or —$CH_2$; n and m are each an integer from 0 to 6 inclusive, or pharmaceutically acceptable salts thereof.

The terms "loweralkyl" and "loweralkoxy" as used herein refer to straight or branched chain alkyl radicals containing from 1 to 6 carbon atoms including but not limited to methyl, ethyl, n-propyl, iso-propyl, n-butyl, sec-butyl, t-butyl, 2-methylhexyl, n-pentyl, 1-methylbutyl, 2,2-dimethylbutyl, 2-methylpentyl, 2,2-dimethylpropyl, n-hexyl and the like.

The term "halo" as used herein refers to chloro, bromo, fluoro and iodo.

The term "pharmaceutically acceptable salts" includes nontoxic acid addition salts of the compounds of the invention which are generally prepared by reacting the free base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, and like salts. Also included are metallic salts such as the sodium or potassium salt of the acid.

The present compounds may be administered to warm-blooded animals orally or parenterally. They can generally be administered with a pharmaceutical carrier. The term "pharmaceutical carrier," for the purpose of the present invention, is intended to refer to any medium that is suitable for the preparation of a dosage unit form, and thus includes the tablet medium or a pharmaceutically acceptable vehicle or solvent such as is ordinarily used in the preparation of intravenous or intramuscular solutions.

A pharmaceutical composition containing the compound can be administered to warm-blooded animals in topical, parenteral or oral dosage form. For oral administration, amounts of from about 0.1 to 200 mg./kg. per day per patient are useful, with the total dose of up to 0.5 gm. per day being a suitable range for large animals, including humans. A preferred dosage range is from about 1.0 to 2.0 grams total daily dosage in a single or divided dose.

For all dosage forms, the above exemplified compounds can be placed in capsules, formulated into pills, wafers or tablets in conventional fashion together with pharmaceutical carriers well known in the art. Tablets may be prepared for immediate release of the active compound or they may be made enteric, i.e., whereby the active ingredient is released slowly over a period of several hours from within the intestinal tract. Ointments can be prepared for topical application.

DETAILED DESCRIPTION OF THE INVENTION

Compounds of Formula I can be prepared by the reaction of the appropriate hydrazino compound with acrylonitrile in absence or in the presence of a solvent such as dioxane, tetrahydrofuran, diglyme, methylene chloride and in the presence of a base such as choline, sodium hydroxide, sodium ethoxide, etc., at temperatures varying from room temperature to 150° C.

In order to illustrate the manner in which the above compounds may be prepared and the properties of the compounds, reference is made to the following examples, which, however, are not meant to limit or restrict the scope of the invention in any respect.

EXAMPLE 1

3-[1-(2-Benzoxazolyl)hydrazino]propanenitrile

Procedure (a)

Into a 400 ml. beaker equipped with a stirrer, thermometer dropping funnel and ice bath was placed 85% hydrazine hydrate (60 g.). Into the dropping funnel were placed 2-chlorobenzoxazole (27 g.) and dioxane (25 ml.). This mixture was added to hydrazine hydrate at such a rate that the temperature did not exceed 30° C. Vigorous stirring was maintained through the addition. After the addition was complete, stirring was continued for 15 minutes and the slurry was diluted with water to remove any excess hydrazine. The solid was collected, washed with water and dried at 50° C. overnight to give 2-hydrazinebenzoxazole.

To a stirred suspension of 2-hydrazinebenzoxazole (2.98 g.) in acrylonitrile (13 ml.) were added twenty drops of 50% methanolic solution of choline. The suspension was stirred at 110° for 1 hour. The reaction mixture was poured into ice water, the pH was adjusted to 12 using sodium hydroxide. The precipitate was collected, dried and crystallized from hot benzene-hexane to give 3-[1-(2-benzoxazolyl)hydrazino]propanenitrile, m.p. 169°–170°.

Procedure (b)

2-Hydrazinebenzoxazole (76.2 g.) was dissolved in tetrahydrofuran (500 ml.) at 40° C. To this was added acrylonitrile (38.7 ml.) followed by ten drops of 50% choline-methanol. Stirring was continued for 15 minutes and then the reaction mixture was heated overnight at 65° C. A solution of concentrated hydrochloric acid (42 ml.) in water (63 ml.) was added. All the compound dissolved. The solution was cooled and back basified to pH 12 with sodium hydroxide pellets. The solid which formed was collected, washed with water, dried and crystallized from ethyl acetate to give 3-[1-(2-benzoxazolyl)hydrazino]propanenitrile, m.p. 169°-170°.

Procedure (c)

To a suspension of 2-hydrazinebenzoxazole (92.6 g) in tetrahydrofuran (800 ml) was added acrylonitrile (42.2 g) at room temperature with stirring. A solution of 2N sodium hydroxide (5 ml) was added dropwise at 30° C. The temperature was raised to 60° C. and stirring was continued for 15 minutes. The heating was removed and stirring was continued for an additional 15 minutes at ambient temperature. Water (1500 ml) was added and the mixture cooled to 5° C. The precipitate was filtered, washed with water, dried and crystallized from ethylacetate to give 3-[1-(2-benzoxazolyl)hydrazino]propanenitrile, m.p. 169°-170°.

EXAMPLE 2

When the procedure (c) described in Example 1 is applied to the following 2-chlorobenzoxazole derivatives the following compounds are obtained:

| Starting Compound | Product |
| --- | --- |
| 2,5-dichlorobenzoxazole | 2-[1-(5-chloro-2-benzaxozolyl)-hydrazino]propanenitrile m.p. 143–144° C. |
| 2-chloro-5-methoxybenzoxazole | 3-[1-(5-methoxy-2-benzoxazolyl)hydrazino]propanenitrile m.p. 124–126° C. |
| 2-chloro-6-methoxybenzoxazole | 3-[1-(6-methoxy-2-benzoxazolyl)-hydrazino]propanenitrile m.p. 109–111° C. |
| 2-chloro-5-methylbenzoxazole | 3-[1-(5-methyl-2-benzoxazolyl)-hydrazino]propanenitrile, m.p. 105–107° C. |
| 2-chloro-5-nitrobenzoxazole | 3-[1-(5-nitro-2-benzoxazolyl)-hydrazino]propanenitrile |
| 2-chloro-6-nitrobenzoxazole | 3-[1-(6-nitro-2-benzoxazolyl)-hydrazino]propanenitrile |

EXAMPLE 3

3-[1-(7-Chloro-2-benzoxazolyl)hydrazino]propanenitrile

A mixture of 7-chloro-2-mercaptobenzoxazole (14.8 g.) and phosphorus pentachloride (29.2 g.) was heated at 160°-170° under reflux for 3 hours. The flask was fitted with a distilling head and the product was distilled in vacuo. The first two fractions were unreacted phosphorus chloride. Afterwards, the product distilled to give 2,7-dichlorobenzoxazole. This compound was reacted with hydrazine using the method described in procedure (a) of Example 1 and then reacted with acrylonitrile using procedure (c) of Example 1 to give 3-[1-(7-chloro-2-benzoxazolyl)hydrazino]propanenitrile, m.p. 114°-115° C.

EXAMPLE 4

When the procedure described in Example 3 is applied to the following 2-mercaptobenzoxazole derivatives, the following compounds are obtained:

| Mercaptobenzoxazoles | Products |
| --- | --- |
| 5-chloro-2-mercaptobenzoxazole | 3-[1-(5-chloro-2-benzoxazolyl)-hydrazino]propanenitrile' m.p. 143–144° C. |
| 5-mercaptomethyl-2-mercaptobenzoxazole | 3-[1-(5-mercaptomethyl-2-benzoxazole)hydrazino]propanenitrile, m.p. 91–92° C. |
| 6-nitro-2-mercaptobenzoxazole | 3-[1-(6-nitro-2-benzoxazolyl)-hydrazino]propanenitrile |
| 5-amino-2-mercaptobenzoxazole | 3-[1-(5-amino-2-benzoxazolyl)-hydrazino]propanenitrile |
| 6-amino-2-mercaptobenzoxazole | 3-[1-(6-amino-2-benzoxazolyl)-hydrazino]propanenitrile |
| 6-acetamido-2-mercaptobenzoxazole | 3-[1-(6-acetamido-2-benzoxazolyl)hydrazino]propanenitrile |
| 5,7-dichloro-2-mercaptobenzoxazole | 3-[1-(5,7-dichloro-2-benzoxazolyl)hydrazino]propanenitrile |
| 6-methyl-5-chloro-2-mercaptobenzoxazole | 3-[1-(6-methyl-5-chloro-2-benzoxazolyl)hydrazino]propanenitrile, m.p. 151–152° C. |
| 5-fluoro-2-mercaptobenzoxazole | 3-[1-(5-fluoro-2-benzoxazole)hydrazino]propanenitrile, m.p. 112–114° C. |
| 6-fluoro-2-mercaptobenzoxazole | 3-[1-(6-fluoro-2-benzoxazole)-hydrazino]propanenitrile |
| 5-cyano-2-mercaptobenzoxazole | 3-[1-(5-cyano-2-benzoxazolyl)-hydrazino]propanenitrile, m.p. 159–160° C. |
| 5-acetamido-2-mercaptobenzoxazole | 3-[1-(5-acetamido-2-benzoxazolyl)hydrazino]propanenitrile |
| 5,7-dimethyl-2-mercaptobenzoxazole | 3-[1-(5,7-dimethyl-2-benzoxazolyl)hydrazino]propanenitrile, m.p. 103–105° C. |
| 5-ethyl-2-mercaptobenzoxazole | 3-[1-(5-ethyl-2-benzoxazolyl)-hydrazino]propanenitrile, m.p. 110–111° C. |
| 5-trifluoromethyl-2-mercaptobenzoxazole | 3-[1-(5-trifluoromethyl-2-benzoxazolyl)hydrazino]propanenitrile; m.p. 146–147° |
| 7-methyl-2-mercaptobenzoxazole | 3-[1-(7-methyl-2-benzoxazolyl)-hydrazino]propanenitrile, m.p. 113–114° C. |
| 4-methyl-2-mercaptobenzoxazole | 3-[1-(4-methyl-2-benzoxazole)-hydrazino]propanenitrile, m.p. 106–107° C. |
| 5-chloro-7-methyl-2-mercaptobenzoxazole | 3-[1-(5-chloro-7-methyl-2-benzoxazolyl)hydrazino]propanenitrile, m.p. 140–142° C. |
| 6-methyl-2-mercaptobenzoxazole | 3-[1-(6-methyl-2-benzoxazolyl)-hydrazino]propanenitrile, m.p. 172–173° C. |

EXAMPLE 5

3-[1-(4,5,7-Trimethyl-2-benzoxazolyl)hydrazino]propanenitrile

To a mixture of aniline (3.72 g.) in ice (40 g.) was added concentrated hydrochloric acid (10.3 ml.). To the solution was added sodium nitrite (2.76 g.) in portions at −5° C. to give phenyldiazonium salt.

The solution of phenyldiazonium was added dropwise under nitrogen to a cold stirred solution (0° C.) of 3,4,6-trimethylphenol (5.44 g.) in 10% aqueous sodium hydroxide solution (43 ml.). The 2-benzeneazo-3,4,6-trimethylphenol precipitated as a deep brown solid. This was filtered, washed with water and dried to give amorphous solid, m.p. 86°-88° C.

To a mixture of 2-benzeneazo-3,4,6-trimethylphenol (7.8 g.) in an 85% potassium hydroxide solution (200 ml.), heated at 80° C. was added portionwise sodium hydrosulfite (20 g.) and heated under reflux for 3 hours. The reaction mixture was cooled to room temperature and acidified to pH 6.0 with concentrated hydrochloric acid. A solid of 2-amino-3,4,6-trimethylphenol precipitated. This was filtered, washed with water and dried, m.p. 159°-161° C. 2-Amino-3,4,6-trimethylphenol (3.39 g.) in ethanol (75 ml.) was treated with potassium ethylxanthate (4.3 g.). The solution was heated under reflux for 3 hours and cooled at room temperature. Acidification with acetic acid (5 ml.) preciptated a solid. This was filtered, washed with water and dried to give 2-mercapto-4,5,7-trimethylbenzoxazole, m.p. 255°-260° C.

The 2-mercapto-4,5,7-trimethylbenzoxazole was converted into 3-[1-(4,5,7-trimethyl-2-benzoxazolyl)-hydrazino]propanenitrile using the method described in Example 3. The product was obtained as white platelets, m.p. 146°-147° C.

EXAMPLE 6

3-[1-(4,5,6-Trimethyl-2-benzoxazolyl)hydrazino]-propanenitrile

When the procedure described in Example 1 was applied to 3,4,5-trimethylphenol, 3-[1-(4,5,6-trimethyl-2-benzoxazolyl)hydrazino]propanenitrile was obtained, m.p. 143°-144° C. after crystallization from ethanol.

EXAMPLE 7

When procedure (c) described in Example 1 was applied to methacrylonitrile and crotononitrile, 3-[1-(2-benzoxazolyl)hydrazino]-2-methylpropanenitrile, m.p. 101°-103° and 3-[1-(2-benzoxazolyl)hydrazino]-3-methylpropanenitrile, m.p. 94°-96°, respectively were obtained.

EXAMPLE 8

3-[1-(2-Benzoxazolyl)hydrazino]-2,2-dimethyl-propanenitrile

A solution of 2,2-dimethyl-2-cyanoacetaldehyde (9.4 g.) in ethanol (100 ml.) is added dropwise to a solution of hydrazine hydrate (40 g.) in ethanol (400 ml.), heated under reflux over a period of 3 hours. The solvent and excess of reagent are removed in vacuo to give 2,2-dimethyl-2-cyanoacetaldehyde hydrazone. This is dissolved in ethanol (100 ml.) and treated at room temperature with sodium borohydride (3.7 g.). The reaction mixture is stirred for two hours, acidified with acetic acid to pH 5, diluted with water and extracted with methylene chloride. The organic phase is dried and concentrated in vacuo to give 2,2-dimethyl-3-hydrazinopropanenitrile. A solution of 2-chlorobenzoxazole (15.3 g.) in dioxane (150 ml.) is added dropwise at 0° C. to a solution of 2,2-dimethyl-3-hydrazino-propanenitrile (11.3 g.) and triethylamine (10.1 g.) in dioxane (400 ml.). Stirring is continued overnight at room temperature. The precipitate is filtered and the filtrate concentrated in vacuo. The residue is washed with water and crystallized to give 3-[1-(2-benzoxazolyl) hydrazino)-2,2-dimethylpropanenitrile.

EXAMPLE 9

4-[1-(2-Benzoxazolyl)hydrazino]butanenitrile

A solution of 3-hydrazino-1-propanol (18.0 g.) and triethylamine (20.2 g.) in dioxane (300 ml.) was treated dropwise with a solution of 2-chlorobenzoxazole (30.8 g.) in dioxane (40 ml.) at 10° C. The reaction was then stirred at room temperature overnight. The precipitate was filtered and the filtrate concentrated in vacuo. The residue was crystallized from boiling benzene to give 4-[1-(2-benzoxazolyl)hydrazino]butanol, m.p. 87°-90° C.

A mixture of 4-[1-(2-benzoxazolyl)hydrazino]butanol (10 g.), benzaldehyde (5.6 g.), and two crystals of p-toluenesulfonic acid monohydrate in benzene (130 ml.) was heated under reflux and with water separator overnight. The cooled reaction mixture was filtered. The obtained solid was triturated with hexane to give 4-[1-(2-benzoxazolyl) hydrazino]butanol benzylidene, m.p. 115°-118° C.

A solution of 4-[1-(2-benzoxazolyl)hydrazino]butanol benzylidene (2.38 g.) and carbon tetrabromide (3.33 g.) in methylene chloride (30 ml.) cooled to 0° C. was treated portionwise with triphenylphosphine (3.15 g.). At the end of the addition the reaction was stirred for additional five minutes, then concentrated in vacuo. The residue was triturated with methylene chloride. The solid was filtered to give 4-[1-(2-benzoxazolyl)hydrazino]butylbromide benzylidene, m.p. 170°-182° C. A solution of 4-[1-(2-benzoxazolyl)hydrazino]butylbromide benzylidene (1.2 g.) and sodium cyanide (0.7 g.) in dry DMF (20 ml.) was stirred at room temperature for ten minutes and then heated in an oil bath at 60° C. for two hours. The reaction mixture stood at room temperature overnight, then poured into ice water. The solid was filtered and crystallized from ethanol to give 4-[1-(2-benzoxazolyl)hydrazino]butanenitrile benzylidene, m.p. 124°-125° C.

A mixture of 4-[1-(2-benzoxazolyl)hydrazino]-butanenitrile benzylidene (1.5 g.) and hydrazine hydrate (2.5 g.) in ethanol (40 ml.) is heated under reflux with stirring overnight. The reaction mixture is cooled and diluted with ice water. The solid is filtered and dried to give 4-[1-(2-benzoxa- zolyl)hydrazino]butanenitrile.

EXAMPLE 10

When the procedure described in Example 9, wherein 4-hydrazino-10-butanol and 5-hydrazino-1-pentanol are used in place of 3-hydrazino-1-propanol, 5-[1-(2-benzoxazolyl)-hydrazino]pentanenitrile and 5-[1-(2-benzoxazolyl)-hydrazino]hexanenitrile respectively are obtained.

EXAMPLE 11

4[1-(5-Methylsulfoxide-2-benzoxazolyl)hydrazino]-propanenitrile and

4-[1-(5-methylsulfone-2-benzoxazolyl)hydrazino]propane nitrile

To a solution of 4-[1-(5-methylmercapto-2-benzoxazolyl)hydrazino]-propane nitrile (2.02 g) in methylene chloride (50 ml) was added a solution of m-chloroperbenzoic acid (2 g) in methylene chloride. The mixture was stirred at room temperature for 4 hours, then was extracted with aqueous sodium bicarbonate solution. The organic phase was dried over sodium sulfate and concentrated. The residue was purified by column chromatography to give 4-[1-(5-methyl-sulfoxide-2-benzoxazolyl)-hydrazino]propanenitrile, m.p. 124°-126° C. and 4-[1-(5-methylsulfone-2-benzoxazolyl)hydrazino]propanenitrile, m.p. 165°-167° C.

EXAMPLE 12

3-[1-(2-indolyl)hydrazino]propanenitrile

A mixture of oxindole (1.33 g.), phosphorous oxychloride (4.59 g.) and triethylamine (1.01 g.) was heated under reflux for four hours. The excess of reagents were removed in vacuo and the oily residue was dissolved in dioxane (50 ml.). The solution was added to hydrazine hydrate (2.5 ml.) in dioxane (50 ml.) and heated under reflux for ten hours. The solvent and excess of reagent were removed in vacuo and the product was crystallized from ethanol-ether to give 2-indolyl hydrazine, m.p. 165°-167° C.

To a solution of 2-indolyl hydrazine (1.47 g.) in THF (100 ml.) was added acrylonitrile (0.75 g.) and five drops of 2N sodium hydroxide solution. The reaction mixture was heated under reflux for eight hours and then concentrated in vacuo. The residue was dissolved in ethanol, treated with activated charcoal, filtered and cncentrated again to give 3-[1-(2-indolyl)hydrazino]-propanenitrile, crystallized from ether-ethanol, m.p. 120°–122° C.

EXAMPLE 13

3-[1-(2-benzthiazolyl)hydrazino]propanenitrile

When procedure (c) described in Example 1 was applied to 2-hydrazinobenzthiazole, 3-[1-(2-benzthiozolyl)hydrazino]propanenitrile, m.p. 111°–113° C. was obtained.

EXAMPLE 14

When the procedure described in Example 13 is applied to methacrylonitrile and to crotonnitrile, 3-[1-(2-benzthiazolyl)hydrazino-2-methyl]propanenitrile and 3-[1-(2benzthiazolyl)hydrazino]-3-methylpropane nitrile, m.p. 119°–120° C. respectively are obtained.

The compounds of the present invention have anti-inflammatory activity and inhibitory effect against Type III hypersensitivity reaction. These compounds are useful for the therapy of osteoarthritis, rheumatoid arthritis, other inflammatory conditions, Type III hypersensitivity diseases and in diseases in which polymorphonuclear leukocytes accumulation contributes to the pathology.

The anti-inflammatory activity of these compounds was established by using a modification of the carrageenin pleurisy assay described in Vinegar et al. Proc. Soc. Exp. Biol. Med. 143:711 (1973). Table 1 shows the reduction in accumulation of exudate volume and leukocytes.

TABLE I

| Compound | Dose | % Inhibition Volume exudates | Cells |
|---|---|---|---|
| Phenylbutazone | 100 | 59 | 13 |
| 3-[1-(2-benzoxazolyl)hydrazino]-propane nitrile | 100 | 61 | 39 |

The ability of these compounds to inhibit Type III hypersensitivity reactions was demonstrated using the reverse passive Arthus assay as described by Carter and Krause Fed. Proc. 35, 774 (1976). Each compound was administered orally to a group of four animals.

The Arthus reaction represents one of the oldest and best studied models of immunological injury. It is produced by the injection of antigen locally into a hyperimmunized animal or by the injection of a small amount of antibody into the skin of an animal that has just previously been given a large amount of soluble antigen intravenously. In both cases the antigen and antibody become deposited in the walls of small venules. Plasma complement is rapidly bound and activated. Within a few hours neutrophils (PMNs) accumulate resulting in distruption of the basement membrane of vessel walls and marked edema and hemorrage in the surrounding tissue.

Although the etiology of rheumatoid arthritis remains obscure, it is almost certain that immunological mechanisms play in important role in the pathogenesis of this disease. Therefore, inflammation induced by immunological reactions, which are believed to be important in the inflammatory processes of rheumatoid arthritis, make particularly desirable tools for the screening of potential anti-inflammatory agents. The usefulness of such a model depends upon how closely it represents the underlying pathological mechanisms of rheumatoid arthritis.

Based upon currently available evidence, a plausible sequence of events leading to the joint lesions in rheumatoid arthritis can be constructed. An initiating antigen, perhaps a transient synovial infection, results in an immune response and retention of the antigen within the joint structure. The interaction of antigen with developing antibodies results in the deposition of immune complexes. These complexes may fix and activate complement, causing the generation of a number of phlogistic and chemotactic substances. Phagocytosis of the complexes by attracted polymorphonuclear leukocytes (PMNs) leads to the release of lysosomal constituents. The enzymes released from lysosomes can erode articular cartilage and produce inflammation in the joint. The striking resemblance of these events to the Arthus phenomenon point to the utility of the Arthus reaction as a screen for anti-inflammatory compounds.

The reserve passive Arthus reaction test in rats is conducted as follows: Male Sprague-Dawley rats weighing approximately 130–160 g. are used, 4 rats per group. All animals are injected intravenously with 0.5 ml. 0.075% Bovine Serum Albumin (B.S.A.)+2% Evans Blue solution. Each rat then receives an oral dose of drug; one drug is administered per group.

Thirty minutes subsequent to drug dosing, each animal is injected intradermally with 0.05 ml. 1.44% Anti-B.S.A. into the dorsal skin. Four hours later the animals are sacrificed, the dorsal skin reflexed, and the lesion excised. Two perpendicular diameters of each lesion are measured. The average diameters of the lesions from the treated groups are compared with the average diameters from the control group to determine any drug effect.

Table II shows the percentage of reduction in lesion area produced by several representative compounds.

TABLE II

| Compound | Dose mg/kg | % Inhibition of lesion of dermal Arthus reaction |
|---|---|---|
| Phenylbutazone | 100 | inactive |
| 3-[1-(2-benzoxazolyl)-hydrazino]propane-nitrile | 100 | 68 |
| 3-[1-(5-methyl-2-benzoxazolyl)hydrazino]propanenitrile | 100 | 70 |
| 3-[1-(5-methoxy-2-benzoxazolyl)hydrazino]propanenitrile | 100 | 67 |
| 3-[1-(5-fluoro-2-benzoxazolyl)hydrazino]propanenitrile | 100 | 55 |
| 3-[1-(5-cyano-2-benzoxazolyl)hydrazino]propanenitrile | 100 | 66 |
| 3-[1-(5-mercapto-methyl-2-benzoxazolyl)hydrazino]propanenitrile | 100 | 40 |
| 3-[1-(7-methyl-2-benzoxazolyl)hydrazino]propanenitrile | 100 | 47 |
| 3-[1-(6-methyl-2-benzoxazolyl)hydrazino]propanenitrile | 100 | 58 |
| 3-[1-(7-chloro-2- | 100 | 48 |

TABLE II-continued

| Compound | Dose mg/kg | % Inhibition of lesion of dermal Arthus reaction |
|---|---|---|
| benzoxazolyl)hydrazino]propanenitrile | | |
| 3-[1-(5,7-dimethyl-2-benzoxazolyl)hydrazino]propanenitrile | 100 | 59 |
| 3-[1-(5-chloro-2-6-methyl-2-benzoxazolyl)hydrazino]propanenitrile | 100 | 76 |
| 3-[1-(4,5,7-trimethyl-2-benzoxazolyl)hydrazino]propanenitrile | 100 | 55 |
| 3-[1-(5-trifluoromethyl-2-benzoxazolyl)-hydrazino]propanenitrile | 100 | 48 |
| 3-[1-(2-benzoxazolyl)-hydrazino]-2-methylpropane | 100 | 45 |
| 3-[1-(2-benzoxazolyl)-hydrazino]-3-methylpropanenitrile | 100 | 48 |
| 3-[1-(4,5,6-trimethyl-2-benzoxazolyl)hydrazino]propanenitrile | 100 | 59 |
| 3-[1-2-benzthiazolyl)hydrazino]propanenitrile | 100 | 59 |

What is claimed is:

1. A compound of the formula

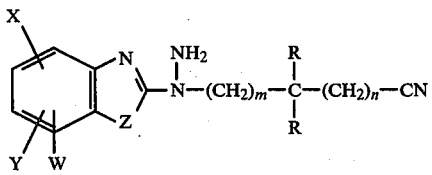

wherein R is hydrogen or loweralkyl; X, Y and W independently of one another denote hydrogen, halogen, loweralkyl, nitro, nitrile, amino, amido, loweralkoxy, lydroxy, mercaptomethyl, or trifluoromethyl, provided that X, Y and W are not simultaneously all nitro or all hydroxy; Z is oxygen; n and m are each an integer from 0 to 6 inclusive; or pharmaceutically acceptable salts thereof.

2. A compound of claim 1 wherein R is hydrogen or loweralkyl; X, Y and W independently of one another denote hydrogen, loweralkyl, trifluoromethyl, nitrile or loweralkoxy; and n and m are each an integer from 0 to 4 inclusive.

3. A compound of claim 2 wherein R is hydrogen or loweralkyl; X is hydrogen, loweralkyl, trifluoromethyl, nitrile or loweralkoxy; Y and W are independently hydrogen or loweralkyl; and n and m are each an integer from 0 to 4 inclusive.

4. A compound of claim 3 wherein R is hydrogen; X is hydrogen, methyl, methoxy, nitrile or trifluoromethyl; Y is hydrogen or methyl; W is hydrogen or methyl; n is 1; and m is 0.

5. A compound of claim 4 wherein R is hydrogen, X is trifluoromethyl; Y is hydrogen, W is hydrogen; n is 1; and m is 0.

6. A compound of claim 4 wherein R is hydrogen, X is methyl, Y is hydrogen; W is hydrogen; n is 1; and m is 0.

7. A compound of claim 4 wherein R is hydrogen; X is methoxy; Y is hydrogen; W is hydrogen; n is 1; and m is 0.

8. A compound of claim 4 wherein R is hydrogen; X is nitrile, Y is hydrogen; W is hydrogen; n is 1; and m is 0.

9. The compound 3-[1-(2-benzoxazolyl)hydrazino]-propanenitrile.

10. A method of treating or relieving the symptoms associated with inflammation comprising administering to a patient in need of such treatment a therapeutically effective amount of an anti-inflammatory agent of the formula

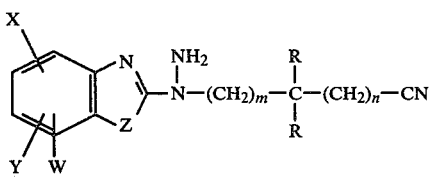

wherein R is hydrogen or loweralkyl; X, Y and W independently of one another denote hydrogen, halogen, loweralkyl, nitro, nitrile, amino, amido, loweralkoxy, hydroxy, nitrile, methylsulfone, methylsulfoxide, mercaptomethyl, or trifluoromethyl, provided that X, Y and W are not simultaneously all nitro or all hydroxy; Z is oxygen; n and m are each an integer from 0 to 6 inclusive, or pharmaceutically acceptable salts thereof.

11. The method of claim 10 wherein R is hydrogen or loweralkyl; X, Y and W independently of one another denote hydrogen, loweralkyl, trifluoromethyul, nitrile or loweralkoxy; and n and m are each an integer from 0 to 4 inclusive.

12. The method of claim 11 wherein R is hydrogen or loweralkyl; X is hydrogen, loweralkyl, trifluoromethyl, nitrile or loweralkoxy; Y and W are independently hydrogen or loweralkyl; and n and m are each an integer from 0 to 4 inclusive.

13. The method of claim 12 wherein R is hydrogen, X is hydrogen, methyl, methoxy, nitrile or trifluoromethyl; Y is hydrogen or methyl; W is hydrogen or methyl; n is 1; and m is 0.

14. The method of claim 13 wherein R is hydrogen; X is hydrogen; Y is hydrogen; W is hydrogen; n is 1; and m is 0.

15. A pharmaceutical composition useful for the treatment of inflammatory conditions which comprises a compound of the formula

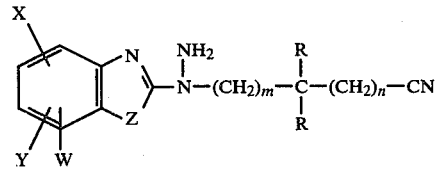

wherein R is hydrogen or loweralky; X, Y and W independently of one another denote hydrogen, halogen, loweralky, nitro, amino, amido, loweralkoxy, hydroxy, nitrile, methylsulfone, methylsulfoxide, methylmercapto, or trifluoromethyl, provided that X, Y and W are not simultaneously all nitro or all hydroxy; Z is oxygen; n and m are each an integer from 0 to 6 inclusive, or pharmaceutically acceptable salts thereof, and a pharmaceutically acceptable carrier.

16. The composition of claim 15 wherein R is hydrogen or loweralkyl; X, Y and W independently of one another denote hydrogen, trifluoromethyl, nitrile, loweralkyl or loweralkoxy; and n and m are each an integer from 0 to 4 inclusive.

17. The composition of claim 16 wherein R is hydrogen or loweralkyl; X is hydrogen, trifluoromethyl, nitrile or loweralkoxy; Y is hydrogen or loweralkyl; W is hydrogen or loweralkyl; and n and m are each an integer from 0 to 4 inclusive.

18. The composition of claim 17 wherein R is hydrogen; X is hydrogen, methyl, methoxy, nitrile or trifluoromethyl; Y is hydrogen or methyl; W is hydrogen or methyl; n is 1 and m is 0.

19. The composition of claim 18 wherein R is hydrogen; X is hydrogen; Y is hydrogen; W is hydrogen; n is 1 and m is 0.

* * * * *